United States Patent
Song et al.

(10) Patent No.: US 9,072,817 B2
(45) Date of Patent: Jul. 7, 2015

(54) BONE-REPAIR COMPOSITION

(75) Inventors: Seok Beom Song, Seongnam (KR); Jung Won So, Seongnam (KR); Hyun Seung Ryu, Yongin (KR); Byoung Suck Kim, Seoul (KR)

(73) Assignee: CG BIO Co., Ltd., Kyunggi-Do (KR)

( * ) Notice: Subject to any disclaimer, the term of this patent is extended or adjusted under 35 U.S.C. 154(b) by 103 days.

(21) Appl. No.: 13/379,758

(22) PCT Filed: Jan. 27, 2010

(86) PCT No.: PCT/KR2010/000486
§ 371 (c)(1),
(2), (4) Date: Dec. 21, 2011

(87) PCT Pub. No.: WO2010/150958
PCT Pub. Date: Dec. 29, 2010

(65) Prior Publication Data
US 2012/0093895 A1    Apr. 19, 2012

(30) Foreign Application Priority Data

Jun. 26, 2009    (KR) .................. 10-2009-0057747

(51) Int. Cl.
*A61K 9/00* (2006.01)
*A61L 27/36* (2006.01)
*A61L 27/50* (2006.01)

(52) U.S. Cl.
CPC ........... *A61L 27/365* (2013.01); *A61L 27/3608* (2013.01); *A61L 27/3687* (2013.01); *A61L 27/50* (2013.01); *A61L 2430/02* (2013.01)

(58) Field of Classification Search
CPC ..................................................... A61K 9/00
See application file for complete search history.

(56) References Cited

U.S. PATENT DOCUMENTS

2007/0178158 A1*    8/2007    Knaack et al. ................ 424/484

FOREIGN PATENT DOCUMENTS

| JP | 03-125151 B2 | 11/2000 |
| JP | 2002-501786 A | 1/2002 |
| WO | 2004/091435 A2 | 10/2004 |

OTHER PUBLICATIONS

Jang, J.W., et al., Preparation and Characterization of Sponge Using Demineralized Bone Particle; Polymer (Korea), vol. 33, No. 2; pp. 104-110 (2009).
PCT/KR2010/000486 International Search Report; Nov. 4, 2010; 3 pages.

* cited by examiner

*Primary Examiner* — Karen Cochrane Carlson
*Assistant Examiner* — Natalie Moss
(74) *Attorney, Agent, or Firm* — Lathrop & Gage LLP

(57) ABSTRACT

The present invention relates to a bone-repair composition comprising a micro-pulverized demineralized bone matrix; a nonmicro-pulverized demineralized bone matrix; and a hydrating material. The bone-repair composition of the present invention provides easier injectability and shape-maintenance (handling), and exhibits excellent bone-repairing effects due to a large surface area of the micro-pulverized demineralized bone matrix and an early release of the bone growth factors, compared with conventional compositions comprising the nonmicro-pulverized demineralized bone matrix alone. It also has an advantage of being biocompatible and harmless to the human body because there is no use of synthetic materials.

13 Claims, 1 Drawing Sheet

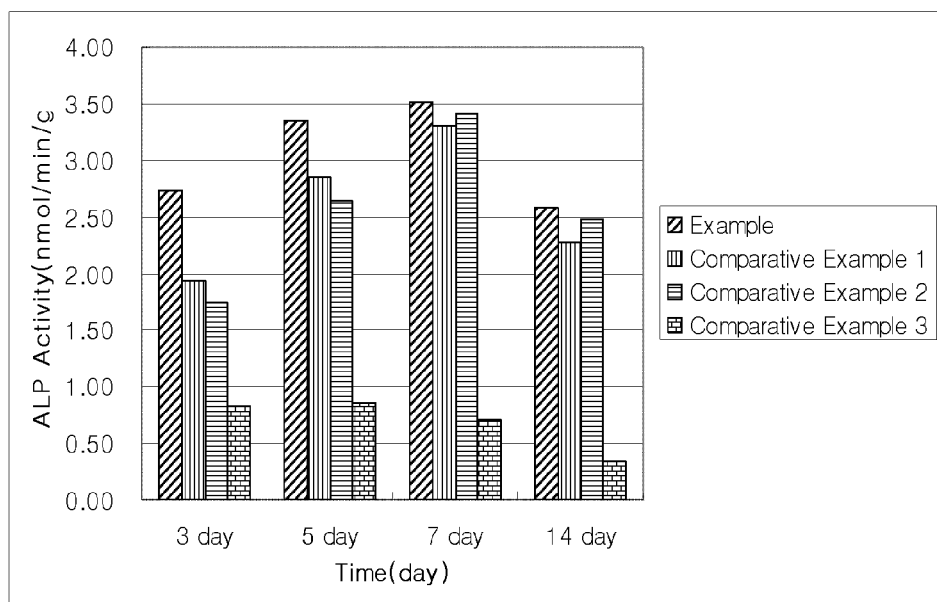

BONE-REPAIR COMPOSITION

TECHNICAL FIELD

The present invention relates to a bone-repair composition comprising a micro-pulverized demineralized bone matrix; a nonmicro-pulverized demineralized bone matrix; and a hydrating material.

BACKGROUND ART

Demineralized bone matrix (DBM) refers to a bone whose minerals have been removed by adding it to an acid. Demineralized bone matrix mostly consists of highly cross-linked collagen and comprises the remaining non-collagenic proteins such as TGF-β, PDGF, osteopontin, osteonectin, bone morphogenetic protein (BMP) and the like.

When the demineralized bone matrix was incorporated (filled) into a mouse muscle, an ectopic bone formation was observed in the incorporated site. This experiment proved that in order for a bone to grow, a material that can induce undifferentiated cells among a group of bone-forming cells to be differentiated should exist in the bone matrix. BMP is such a protein substance existing in the bone matrix (Urist, M R, Strates, B S, bone morphogenetic protein, J. Dental Res. 50:1392-1406, 1971). BMP can be separated from the bone or prepared through the recombinant gene technique.

BMP is a group of proteins that belong to the TGF-β superfamily and was classified based on its ability to induce bone formation (Wozney, J M, Science 242:1528-1534, 1988). The BMP family can be classified into BMPs such as BMP-2 and BMP-4; osteogenetic proteins (OPs) such as OP-1 (or BMP-7), OP-2 (or BMP-8), BMP-5, BMP-6 and Vgr-1; cartilage-derived morphogenetic proteins (CDMPs) such as CDMP-1, BMP-14 and GDF-5; growth/differentiation factors (GDFs) such as GDF-1, GDF-3, GDF-8, GDF-11, GDF-12 and GDF-14; and a subfamily such as BMP-3, osteogenin, BMP-9, GDF-2 and BMP-10.

Various compositions have been used for healing damaged bone tissue. They can act as a framework to support new bone growth and provide growth factors for new bone-growth induction. U.S. Pat. No. 4,394,370 to Jefferies disclosed a tissue-healing composition comprising a recombinant collagen, a demineralized bone matrix and BMP. U.S. Pat. No. 4,440,750 to Glowacki et al. disclosed a hydrating composition consisting of a recombinant collagen and a demineralized bone matrix.

However, the bone-repair efficacy of these compositions is low because the bone growth factors are not released in the early stage but trapped within the highly cross-linked collagen network of the demineralized bone matrix and slowly released as collagen components degrade. As an alternative to such a slow release, a method for separating the bone growth factors from the demineralized bone matrix was suggested (U.S. Pat. No. 7,132,110). However, a number of steps such as extraction, purification, mixing with a dispersion solvent or combination with another carrier are required for such a separation. In addition, it has the disadvantage of causing damage to the bone growth factors and collagen during the separation process.

Furthermore, when the demineralized bone matrix in a powder state is used alone, it is impossible to inject and difficult to maintain and modify the shape; thus, handling is problematic. Thus, in order to provide better injectability, and shape-maintenance and modification properties, a connection with other substances has been raised. Up to now, combination products with an organic polymer such as gellatin, glycerol, poloxamer and hyaluronic acid have been reported, but they did not satisfy all of injectability, shape-maintenance (handling), content and biocompatibility.

Thus, there is an ever-increasing need to develop a bone-repair composition that can release the bone growth factors in the early stage, can be harmless to the human body and can improve injectability and shape-maintenance (handling) of the demineralized bone matrix.

DISCLOSURE OF INVENTION

Technical Problem

The present inventors have performed continuous study on new bone-repair compositions that can resolve problems caused by the conventional compositions as above. As a result, they discovered that if a micro-pulverized demineralized bone matrix and a hydrating material are added to the nonmicro-pulverized demineralized bone matrix to prepare a composition, the thus-prepared composition provides easier injectability and shape-maintenance (handling), and exhibits excellent bone-repairing effects due to a large surface area of the micro-pulverized demineralized bone matrix and an early release of the bone growth factors, compared with conventional compositions comprising the nonmicro-pulverized demineralized bone matrix alone, whereby the present inventon has been completed.

Solution to Problem

To solve the above technical problem, the present invention provides a bone-repair composition comprising a micro-pulverized demineralized bone matrix; a nonmicro-pulverized demineralized bone matrix; and a hydrating material.

Advantageous Effects of Invention

The bone-repair composition of the present invention provides easier injectability and shape-maintenance (handling), and exhibits excellent bone-repairing effects due to a large surface area of the micro-pulverized demineralized bone matrix and an early release of the bone growth factors, compared with conventional compositions comprising the non-micro-pulverized demineralized bone matrix alone. It is also biocompatible and harmless to the human body because there is no use of synthetic materials. Furthermore, since there is no need to additionally separate the bone growth factors from the demineralized bone matrix, there is no need to be concerned about the damage to the bone growth factors and collagen which could occur during the conventional separation process.

BRIEF DESCRIPTION OF DRAWINGS

FIG. 1 is a graph which shows the results of alkaline phosphatase (ALP) measurement that was performed for Example 1 and Comparative Examples 1 to 3 of the present invention.

BEST MODE FOR CARRYING OUT THE INVENTION

The present invention provides a bone-repair composition comprising a micro-pulverized demineralized bone matrix; a nonmicro-pulverized demineralized bone matrix; and a hydrating material.

If the term "demineralized bone matrix" is used herein instead of the terms "micro-pulverized demineralized bone matrix" and "unmicro-pulverized demineralized bone matrix," it refers to both the micro-pulverized demineralized bone matrix and the nonmicro-pulverized demineralized bone matrix.

There is no limit on the kind of demineralized bone matrix that can be used for the bone-repair composition of the present invention. A commercially available demineralized bone matrix can be purchased and used as is, or a bone derived from mammals can be prepared according to the known methods to obtain a demineralized bone matrix (Russell et al., Orthopedics 22 (5) 524-531, 1999) and then used.

According to the known method for preparing a demineralized bone matrix, a compact bone is collected from which soft tissues are removed. Protein and lipid are removed from the bone using an organic solvent or a surfactant, and minerals are removed using an acid. The resulting bone is lyophilized. It is known that the damage to the growth factors in the bone can be lessened if the process for preparing the demineralized bone matrix is carried out under refrigeration (1 to 10° C.).

It is also known that the telopeptide region in the bone matrix collagen, which is known as an immune response-triggering region and known to form a cross-linking between chains, can be removed if the bone matrix is treated with an enzyme such as pepsin, trypsin, chymotrypsin or papain. Through treatment with such an enzyme, the immune response can be decreased, and the solubility of collagen can be increased (G. Khang, Polymer, 33 (2) 104-110, 2009).

Thus, the demineralized bone matrix used for the bone-repair composition of the present invention is preferably one that has been treated with an enzyme. The enzyme used for the treatment is preferably one or more selected from the group consisting of pepsin, trypsin, chymotrypsin and papain. In addition, the demineralized bone matrix is preferably one that has been prepared under refrigeration at 1 to 10° C.

In the demineralized bone matrix used for the bone-repair composition of the present invention, the amount of residual calcium is generally 0.01 to 8%. If the amount exceeds 8%, it may cause the problem of inhibiting the release of the growth factors from the demineralized bone. Thus, the amount of residual calcium is preferably 8% or less and most preferably 2% or less.

As used herein, the term "micro-pulverized" refers to grinding the particles so that 50% or more of the particles have a particle size of about 250 μm or less. Thus, as used herein, the term "micro-pulverized demineralized bone matrix" refers to a demineralized bone matrix that has been pulverized so that 50% or more of which has a particle size of about 250 μm or less. On the other hand, the term "nonmicro-pulverized demineralized bone matrix" refers to a demineralized bone matrix, 50% or more of which has a particle size of about 250 μm or more.

In the bone-repair composition of the present invention, a suitable particle size of the micro-pulverized demineralized bone matrix is 0.05 to 500 μm and preferably 0.05 to 250 μm. A suitable particle size of the nonmicro-pulverized demineralized bone matrix is 100 to 2000 μm, preferably 250 to 2000 μm and most preferably 250 to 710 μm.

The bone-repair composition of the present invention is characterized by comprising a hydrating material in addition to the micro-pulverized demineralized bone matrix and the nonmicro-pulverized demineralized bone matrix. Any commercially available hydrating materials can be used for the composition of the present invention. Preferably, one or more selected from the group consisting of distilled water, saline solution, concentrated saline solution and ion solution can be used for the hydrating material.

In one embodiment, the hydrating material may contain a liquid polyhydroxy compound, examples of which include glycerol or glycerol ester.

In another embodiment, the hydrating material may contain a biocompatible binder. Preferable examples of the biocompatible binder are one or more selected from the group consisting of fibrin adhesive, fibrinogen, thrombin, mussel adhesive protein, silk, elastin, collagen, casein, gellatin, albumin, keratin, chitin and chitosan. Other preferable examples of the biocompatible binder are one or more selected from the group consisting of starch, polylactic acid, polyglycolic acid, polylactic-co-glycolic acid, polydioxanone, polycaprolactone, polycarbonate, polyoxoester, polyamino acid, poly-anhydride, polyhydroxybutylate, polyhydroxyvalerate, poly (propylene glycol-co-fumaric acid), tyrosine-based-polycarbonate, polyvinylpyrrolidone, cellulose, ethyl cellulose and carboxy methyl cellulose.

In another embodiment, the hydrating material may additionally contain one or more selected from the group consisting of antibiotic, vitamins, glucosamine, cytokine and growth factors.

In the bone-repair composition of the present invention, the weight ratio of the micro-pulverized demineralized bone matrix:the nonmicro-pulverized demineralized bone matrix: the hydrating material is 0.1 to 20:1:0.1 to 20, preferably 0.1 to 3:1:1 to 10 and most preferably 0.5 to 1:1:3 to 5.

If the content of the micro-pulverized demineralized bone matrix is less than 0.1 weight based on 1 weight of the non-micro-pulverized demineralized bone matrix, the composition becomes less cohesive, resulting in a crumbly condition and bad shapability. However, if the content is more than 20 weight, the composition degrades quickly, resulting in incomplete bone formation. In addition, if the content of the hydrating material is less than 1 weight based on 1 weight of the nonmicro-pulverized demineralized bone matrix, the composition becomes less cohesive, resulting in a crumbly condition and bad shapability. However, if the content is more than 20 weight, the composition becomes less viscous, resulting in bad shape-maintenance and running.

The bone-repair composition of the present invention may further contain an auxiliary component that can help bone repair, in addition to the micro-pulverized demineralized bone matrix; the nonmicro-pulverized demineralized bone matrix; and the hydrating material. Any commercially available auxiliary components that can help bone repair can be used for the composition of the present invention. Especially, one or more selected from the group consisting of cancellous bone chips, compact bone chips, hydroxyapatite (HA, $Ca_{10}(PO_4)_6(OH)_2$), carbonic acid apatite (CA, $Ca_{10}(PO_4)_6CO_3$), tricalcium phosphate (TCP, $Ca_3(PO_4)_2$), calcium pyrophosphate ($Ca_2P_2O_7$), anorganic bone, dental tooth enamel, aragonite, calcite, nacre, graphite, pyrolytic carbon, calcium-silicate-based bioglass, $Al_2O_3$ and $ZrO_2$ are preferable.

Alkaline phosphatase (ALP) is distributed throughout many organs such as liver, bone, kidney, small intestine and placenta, and a serum ALP mostly originates from bone and liver except for pregnant women. A bone ALP is secreted from osteoblast and is the most generally used marker for bone formation. Since ALP is associated with the activation of osteoblast, it increases with the occurrence of bone repair, such as bone-growth period and bone fracture-recovery period.

In order to confirm the bone-repair effects of the bone-repair composition of the present invention, the present inventors put the composition into C2C12 cell lines (American Type Culture Collection (ATCC), USA), i.e., mouse myoblast cell lines. After culturing the same, the concentration of ALP was measured.

As a result, it was observed that the ALP value of the composition of the present invention is outstandingly higher than that of the compositions of Comparative Examples in the early stage of the culture (days 3 and 5). The high ALP value means that myoblast has been differentiated to osteoblast-like cells. From this result, it was considered that the process of micro-pulverizing the demineralized bone matrix and the process of hydrating the same with the hydrating material could enable early release of the bone growth factors from the demineralized bone matrix and at the same time broaden the surface area of the demineralized bone matrix, whereby the bone-repair efficacy has been improved.

Based on the above, the bone-repair composition of the present invention can be used for all kinds of bone fracture, bone-necrosis disease or bone repair. The conventional demineralized bone powders should be additionally re-hydrated prior to transplantation, whereas the bone-repair composition of the present invention does not need such a re-hydration process and can be directly injected into the region of bone loss or massed by hand and filled into the region.

Hereinafter, the present invention will be described in more detail with reference to the following examples and experimental examples. The examples and experimental examples are provided only to help understanding of the invention but are not to be construed as limiting the scope of the invention.

EXAMPLES

Example 1

A thigh bone was separated from a 1-month-old rabbit and prepared according to the method of Russell et al. (Russell et al., Orthopedics 22 (5) 524-531, 1999) to obtain demineralized bone matrices. Among the demineralized bone matrices, those having a particle size of 250 to 710 µm were used as a nonmicro-pulverized demineralized bone matrix. In addition, the demineralized bone matrices were pulverized, and those having a particle size of 1 to 250 µm were used as a micro-pulverized demineralized bone matrix. Distilled water was used as a hydrating material. The demineralized bone matrices of 1 to 250 µm, the demineralized bone matrices of 250 to 710 µm and distilled water were mixed in the weight ratio of 0.8:1:3.8 to prepare a composition.

Example 2

The demineralized bone matrices of 1 to 250 µm and the demineralized bone matrices of 250 to 710 µm prepared in Example 1 and distilled water were mixed in the weight ratio of 0.1:1:1 to prepare a composition.

Example 3

The demineralized bone matrices of 1 to 250 µm and the demineralized bone matrices of 250 to 710 µm prepared in Example 1 and distilled water were mixed in the weight ratio of 0.3:1:3.8 to prepare a composition.

Example 4

The demineralized bone matrices of 1 to 250 µm and the demineralized bone matrices of 250 to 710 µm prepared in Example 1 and distilled water were mixed in the weight ratio of 0.3:1:5 to prepare a composition.

Example 5

The demineralized bone matrices of 1 to 250 µm and the demineralized bone matrices of 250 to 710 µm prepared in Example 1 and distilled water were mixed in the weight ratio of 0.8:1:1 to prepare a composition.

Example 6

The demineralized bone matrices of 1 to 250 µm and the demineralized bone matrices of 250 to 710 µm prepared in Example 1 and distilled water were mixed in the weight ratio of 0.8:1:5 to prepare a composition.

Example 7

The demineralized bone matrices of 1 to 250 µm and the demineralized bone matrices of 250 to 710 µm prepared in Example 1 and distilled water were mixed in the weight ratio of 3:1:5 to prepare a composition.

Example 8

The demineralized bone matrices of 1 to 250 µm and the demineralized bone matrices of 250 to 710 µm prepared in Example 1 and distilled water were mixed in the weight ratio of 3:1:10 to prepare a composition.

Comparative Example 1

The demineralized bone matrices of 1 to 250 µm and the demineralized bone matrices of 250 to 710 µm prepared in Example 1 were mixed in the weight ratio of 0.8:1 to prepare a composition.

Comparative Example 2

The demineralized bone matrices of 250 to 710 µm prepared in Example 1 and distilled water were mixed in the weight ratio of 1:3.8 to prepare a composition.

Comparative Example 3

The composition obtained in Comparative Example 1 was sterilized with high-pressure steam at 121° C. for 20 min to prepare a composition.

Experimental Example 1

Ten samples of each composition of Examples 1 to 8 and Comparative Examples 1 and 2 were prepared. Each composition was put into a syringe with the same amount, and the piston was pushed into the cylinder by finger to extrude the composition. Injectability was determined considering ease of extrusion and the shape of the extruded composition. In addition, shape-maintenance (handling) was determined after massing the extruded composition by hand. Injectability and shape-maintenance (handling) were evaluated in 5 steps as indicated in Table 1 below, and the results are shown in Table 2 below.

TABLE 1

| Point | Injectability | Shape-maintenance (handling) |
|---|---|---|
| 4 | easily injected and extruded with no cutting | shapable with no break or crack |
| 3 | easily injected but partially cut and cracked | can be massed but partially broken or cracked when shaped |
| 2 | extruded in broken state | cannot be massed when broken |
| 1 | extruded but run | cannot be massed |
| 0 | extruded in powder state | run |

TABLE 2

| Test group | Micro-pulverized DBM | Nonmicro-pulverized DBM | Hydrating material | Injectability | Shape-maintenance (handling) |
|---|---|---|---|---|---|
| Example 1 | 0.8 | 1 | 3.8 | 4 | 4 |
| Example 2 | 0.1 | 1 | 1 | 3 | 3 |
| Example 3 | 0.3 | 1 | 3.8 | 3 | 3 |
| Example 4 | 0.3 | 1 | 5 | 3 | 3 |
| Example 5 | 0.8 | 1 | 1 | 3 | 3 |
| Example 6 | 0.8 | 1 | 5 | 4 | 3 |
| Example 7 | 3 | 1 | 5 | 3 | 3 |
| Example 8 | 3 | 1 | 10 | 3 | 3 |
| Comparative Example 1 | 0.8 | 1 | 0 | 0 | 0 |
| Comparative Example 2 | 0 | 1 | 3.8 | 0 | 0 |

As shown in Table 2 above, the compositions of Examples 1 to 8 exhibited higher evaluation scores in both injectability and shape-maintenance (handling) compared with the compositions of Comparative Examples 1 and 2. From the results, it was understood that the case of adding the micro-pulverized demineralized bone matrix exhibits improved injectability and shape-maintenance (handling), compared with the case of comprising the nonmicro-pulverized demineralized bone matrix alone (Comparative Example 2). In addition, it was understood that going through the hydrating process by further adding distilled water exhibits more improved injectability and shape-maintenance (handling), compared with merely mixing the nonmicro-pulverized demineralized bone matrix and the micro-pulverized demineralized bone matrix (Comparative Example 1).

Furthermore, among Examples 1 to 8, the composition of Example 1 wherein 0.8 weight of the micro-pulverized demineralized bone matrix is added based on 1 weight of the nonmicro-pulverized demineralized bone matrix, exhibited the best injectability and shape-maintenance (handling). It was assumed that this happened because in the case of the composition of Example 1 the hydrated micro-pulverized demineralized bone matrix properly fills the space between the nonmicro-pulverized demineralized bone matrix, and thus the synergistic effects due to mixing of the micro-pulverized demineralized bone matrix and the nonmicro-pulverized demineralized bone matrix are higher.

Experimental Example 2

Ten samples of each composition of Example 1 and Comparative Examples 1 to 3 were prepared. The concentration of ALP was measured using C2C12 cell lines (ATCC, USA). The experimental procedure was as follows.

(1) Cell Culture

C2C12 cell lines were inoculated into a 24-well plate by $5 \times 10^4$ cells/each 2 $cm^2$ well. 50 mg of each composition of Example 1 and Comparative Examples 1 to 3 was added to each well and cultured with a nutrition medium. The nutrition medium was changed every 3 to 5 days. After removing the nutrition medium at 3, 5, 7 and 14 days, ALP was quantitatively analyzed.

(2) ALP Quantitative Analysis

After removing the nutrition medium, the plate was washed with saline solution three times. After adding 400 µl of cell lysis butter (pH 7.5) to each well, freeze-thaw cycles (−70° C. and 37° C.) were carried out three times, and the plate was stirred for 5 min per cycle. 50 µl of the sample (cell lysate suspension 250 µl+enzyme butter 25 µl) and 50 µl of pNPP substrate solution in the ratio of 1:1 were added to a 96-well plate and cultured at 37° C. for 30 min. 50 µl of stopping reagent, in an equivalent amount to the sample and the pNPP solution, was added to stop the reaction. The well plate was quickly mixed for 10 sec, and fluoro-absorbance at 405 nm was measured. The results of ALP quantitative analysis are shown in Table 3 below and illustrated as a graph in FIG. 1 (each value is a mean for the 10 samples).

TABLE 3

| Culture period (day) | Example 1 | Comparative Example 1 | Comparative Example 2 | Comparative Example 3 |
|---|---|---|---|---|
| 3 | 2.74 | 1.94 | 1.74 | 0.82 |
| 5 | 3.34 | 2.84 | 2.64 | 0.86 |
| 7 | 3.51 | 3.31 | 3.41 | 0.71 |
| 14 | 2.58 | 2.28 | 2.48 | 0.34 |

As can be seen from the results shown in Table 3 above, the ALP value of Example 1 was higher than that of Comparative Examples 1 to 3 in the early stage of the culture (days 3 and 5). However, as time passed, the ALP value of Example 1 became similar to that of Comparative Examples 1 and 2. Both Example 1, and Comparative Examples 1 and 2 exhibited higher ALP values for the whole period, compared with Comparative Example 3 wherein the growth factors were destroyed by sterilization with high-pressure steam.

The experiment results indicate that myoblast was differentiated to osteoblast-like cells by the bone growth factors in the demineralized bone matrix. From the results, the existence of the bone growth factors in the demineralized bone matrix which can differentiate cells could be indirectly confirmed.

Furthermore, since the early ALP value of Example 1 was measured to be higher than that of Comparative Examples 1 and 2, it was considered that the process of micro-pulverizing the demineralized bone matrix and the process of hydrating the same with the hydrating material could enable early release of the bone growth factors from the demineralized bone matrix and at the same time broaden the surface area of the demineralized bone matrix, whereby the bone-repair efficacy has been improved.

INDUSTRIAL APPLICABILITY

The bone-repair composition of the present invention provides easier injectability and shape-maintenance (handling), and exhibits excellent bone-repairing effects due to a large surface area of the micro-pulverized demineralized bone matrix and an early release of the bone growth factors, compared with conventional compositions comprising the nonmicro-pulverized demineralized bone matrix alone. The composition is also biocompatible and harmless to the human body because there is no use of synthetic materials. Furthermore, since there is no need to additionally separate the bone growth factors from the demineralized bone matrix, there is no need to be concerned about the damage to the bone growth factors and collagen which could occur during the conventional separation process.

The invention claimed is:

1. A bone-repair composition comprising a micro-pulverized demineralized bone matrix; a nonmicro-pulverized demineralized bone matrix; and a hydrating material,
  wherein the micro-pulverized demineralized bone matrix has a particle size of 0.05 to 250 µm;
  wherein the nonmicro-pulverized demineralized bone matrix has a particle size of 250 to 2000 µm; and
  wherein the weight ratio of the micro-pulverized demineralized bone matrix:the nonmicro-pulverized demineralized bone matrix:the hydrating material is 0.8:1:3.8.

2. The bone-repair composition of claim 1, wherein the hydrating material is one or more selected from the group consisting of distilled water, saline solution, concentrated saline solution and ion solution.

3. The bone-repair composition of claim 2, wherein the hydrating material contains a liquid polyhydroxy compound.

4. The bone-repair composition of claim 3, wherein the liquid polyhydroxy compound is glycerol or glycerol ester.

5. The bone-repair composition of claim 2, wherein the hydrating material contains a biocompatible binder.

6. The bone-repair composition of claim 5, wherein the biocompatible binder is one or more selected from the group consisting of fibrin adhesive, fibrinogen, thrombin, mussel adhesive protein, silk, elastin, collagen, casein, gellatin, albumin, keratin, chitin and chitosan.

7. The bone-repair composition of claim 5, wherein the biocompatible binder is one or more selected from the group consisting of starch, polylactic acid, polyglycolic acid, polylactic-co-glycolic acid, polydioxanone, polycaprolactone, polycarbonate, polyoxoester, polyamino acid, poly-anhydride, polyhydroxybutylate, polyhydroxyvalerate, poly(propylene glycol-co-fumaric acid), tyrosine-based-polycarbonate, polyvinylpyrrolidone, cellulose, ethyl cellulose and carboxy methyl cellulose.

8. The bone-repair composition of claim 2, wherein the hydrating material contains one or more selected from the group consisting of antibiotic, vitamins, glucosamine, cytokine and growth factors.

9. The bone-repair composition of claim 1, further comprising one or more selected from the group consisting of cancellous bone chips, compact bone chips, hydroxyapatite (HA, $Ca_{10}(PO_4)_6(OH)_2$), carbonic acid apatite (CA, $Ca_{10}(PO_4)_6CO_3$), tricalcium phosphate (TCP, $Ca_3(PO_4)_2$), calcium pyrophosphate ($Ca_2P_2O_7$), anorganic bone, dental tooth enamel, aragonite, calcite, nacre, graphite, pyrolytic carbon, calcium-silicate-based bioglass, $Al_2O_3$ and $ZrO_2$.

10. The bone-repair composition of claim 1, wherein the micro-pulverized demineralized bone matrix and the nonmicro-pulverized demineralized bone matrix are those which have been treated with an enzyme.

11. The bone-repair composition of claim 10, wherein the enzyme used for the treatment is one or more selected from the group consisting of pepsin, trypsin, chymotrypsin and papain.

12. The bone-repair composition of claim 1, wherein the micro-pulverized demineralized bone matrix and the nonmicro-pulverized demineralized bone matrix are those which have been prepared under refrigeration at 1 to 10° C.

13. The bone-repair composition of claim 1, wherein the amount of residual calcium in the micro-pulverized demineralized bone matrix and the nonmicro-pulverized demineralized bone matrix is 8% or less.

* * * * *